United States Patent [19]
Satoh et al.

[11] Patent Number: 5,344,831
[45] Date of Patent: Sep. 6, 1994

[54] DIAZABICYCLO DERIVATIVES

[75] Inventors: Hiroaki Satoh, Saitama; Haruhiko Kikuchi, Tsurugashima; Kazuhiko Yamada, Sayama; Ruta Fukutomi, Kawagoe; Masashi Suzuki, Saitama; Koichiro Hagihara, Miyoshimachi; Toru Hayakawa; Takeo Arai, both of Kawagoe; Setsuko Mino, Fujimi, all of Japan

[73] Assignee: Nisshin Flour Milling Co., Ltd., Tokyo, Japan

[21] Appl. No.: 10,145

[22] Filed: Jan. 28, 1993

[30] Foreign Application Priority Data

Jan. 31, 1992 [JP] Japan .................................. 4-016172

[51] Int. Cl.$^5$ .................. C07D 247/02; C07D 487/08; A61K 31/495
[52] U.S. Cl. .................................... 514/249; 544/349
[58] Field of Search ......................... 544/349; 514/249

[56] References Cited

U.S. PATENT DOCUMENTS

| | | | |
|---|---|---|---|
| 4,789,673 | 12/1988 | Donatsch et al. | 514/214 |
| 4,800,225 | 1/1989 | Smith | 546/112 |
| 4,803,199 | 2/1989 | Donatsch et al. | 514/214 |
| 4,910,207 | 3/1990 | Donatsch et al. | 514/305 |
| 5,187,166 | 2/1993 | Kikuchi | 544/349 |
| 5,256,656 | 10/1993 | Kikuchi | 544/105 |

FOREIGN PATENT DOCUMENTS

| | | |
|---|---|---|
| 0469449 | 2/1992 | European Pat. Off. . |
| WO93/01747 | 4/1993 | PCT Int'l Appl. . |
| 2193633 | 2/1988 | United Kingdom . |
| 92/05174 | 4/1992 | World Int. Prop. O. . |

OTHER PUBLICATIONS

The New England Journal of Medicine vol. 305 No. 16 Antiemetic Efficacy of High-Dose Metoclopramide: Randomized Trails With Placebo And Prochlorperazine In Patients With Chemotherapy-Included Nausea and Vomiting Oct. 15, 1981 Richard J. Gralla, et al. pp. 905-909.

Lancet vol. 1 No. 8548 pp. 1461-1463 Prevention of Emesis in Patients Receiving Cytotoxic Drugs By CR3803F A Selective 5-HT, Receptor Antagonist Jun. 27, 1987 D. Cunningham, et al.

The Isomeric 3-Oxo-And 3-Thiagranatanin-7-Ols and Their Derivatives; Reduction of Bicyclic Amino Ketones Related to Tropinone J. Org. Chem 26 pp. 395-407 Feb. 1961 Charles L. Zirkle, et al.

Identification of Serotonin M-Receptor Subtypes and Their Specific Blockade by a New Class of Drugs Nature vol. 316 Jul. 11, 1985 B. P. Richardson, et al. pp. 126-131.

Vagal Sensory Receptors and Their Reflex Effects A. S. Paintal Pharmacological Reviews vol. 33, No. 1 Jan. 1973 pp. 158-211.

*Primary Examiner*—Mark L. Berch
*Attorney, Agent, or Firm*—Oblon, Spivak, McClelland, Maier & Neustadt

[57] ABSTRACT

Diazabicyclo derivatives of formula (I) and pharmaceutically acceptable salts thereof:

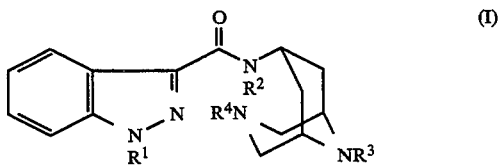

wherein
R is hydrogen, alkyl, alkenyl, alkynyl, cycloalkyl, cycloalkylalkyl, alkoxyalkyl, oxoalkyl, alkoxycarbonylalkyl, alkoxycarbonyl, acyl, dialkylaminoalkyl, hydroxyalkyl, haloalkyl, cyanoalkyl, heterocycloalkyl, aryl, heteroarylalkyl or arylalkyl, the aryl group and the aryl moiety being optionally substituted by alkoxy, nitro, alkyl, amino or halo;

$R^2$ is hydrogen or alkyl;

$R^3$ and $R^4$ may be the same or different and each is hydrogen, alkyl, alkenyl, acyl, alkoxyalkyl or arylalkyl wherein the aryl moiety is optionally substituted by alkoxy, nitro, alkyl, amino or halo;

with the proviso that when $R^2$ is hydrogen and both $R^3$ and $R^4$ are methyl, $R^1$ does not represent hydrogen, alkyl, unsubstituted benzyl or dimethylaminoethyl; having 5-HT$_3$ receptor antagonist activity.

5 Claims, No Drawings

DIAZABICYCLO DERIVATIVES

FIELD OF THE INVENTION

This invention relates to new diazabicyclo derivatives, processes for their preparation and to the pharmaceutical use thereof. More particularly, the invention relates to 3,9-diazabicyclo[3.3.1]nonane derivatives or pharmaceutically acceptable salts thereof which are selective antagonists of 5-HT (serotonin) at $5\text{-HT}_3$ receptors.

BACKGROUND OF THE INVENTION

Nausea and vomiting are serious problems frequently observed in patients receiving a cancer chemotherapeutic agent and radiotherapy. Therefore control of nausea and vomiting is a very important auxiliary treatment for undergoing satisfactory treatment for cancer. Gralla, R. J. et al have reported in *N. Engl. J. Med.* 305, 905-909 (1981) that nausea and vomiting are effectively prevented by intravenous administration of metoclopramide at high dose. However it has been revealed that presently available antiemetics, particularly compounds containing a benzamide structure are associated with adverse reactions such as sedation, ataxia, diarrheas and tasikinesia due to their dopamine-blocking activities and central nerve-depressant activities.

Cunningham, D. et al have reported in The Lancet, 1, 1461-1463 (1987) that specific antagonists of $5\text{-HT}_3$ receptors prevent vomiting and nausea associated with cancer therapy. Thus $5\text{-HT}_3$ receptor antagonists are believed to be anti-emetics which can prevent vomiting and nausea at a lower dose than known agents without adverse reactions associated.

As $5\text{-HT}_3$ receptor antagonists, compounds containing an azabicyclic moiety are known as disclosed in U.S. Pat. Nos. 4,789,673; 4,803,199; 4,910,207; GB 2152049 A; U.S. Pat. No. 4,800,225, GB 2208862 A and European Patent Application 0377967 A2 and compounds containing an imidazole moiety are known as disclosed in GB 2153821 A.

Under such circumstances, it has been desired to develop more selective antagonists of 5-HT at $5\text{-HT}_3$ receptors.

DETAILED DESCRIPTION OF THE INVENTION

We have now found that new diazabicyclo derivatives structurally different from the prior compounds possess a selectively effective antagonism against the effect of 5-HT at $5\text{-HT}_3$ receptors.

Thus the present invention provides in one aspect a compound of formula (I) or a pharmaceutically acceptable salt thereof

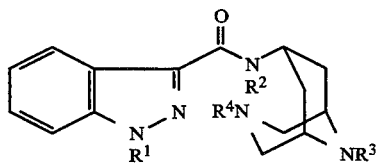

wherein $R^1$ is hydrogen, alkyl, alkenyl, alkynyl, cycloalkyl, cycloalkylalkyl, alkoxyalkyl, oxoalkyl, alkoxycarbonylalkyl, alkoxycarbonyl, acyl, dialkylaminoalkyl, hydroxyalkyl, haloalkyl, cyanoalkyl, heterocycloalkyl, aryl, heteroarylalkyl or arylalkyl, the aryl group and the aryl moiety being optionally substituted by alkoxy, nitro, alkyl, amino or halo;

$R^2$ is hydrogen or alkyl;

$R^3$ and $R^4$ may be the same or different and each is hydrogen, alkyl, alkenyl, acyl, alkoxyalkyl or arylalkyl wherein the aryl moiety is optionally substituted by alkoxy, nitro, alkyl, amino or halo;

with the proviso that when $R^2$ is hydrogen and both $R^3$ and $R^4$ are methyl, $R^1$ does not represent hydrogen, alkyl, unsubstituted benzyl or dimethylaminoethyl.

The aryl group and the aryl moiety in the heteroarylalkyl and arylalkyl may be substituted in either of o-, m- and p-positions by alkoxy preferably $C_1$-$C_6$ alkoxy, nitro, alkyl preferably $C_1$-$C_6$ alkyl, amino or halo. Heteroatoms for heterocycloalkyl, heteroarylalkyl and heteroaryl are selected from oxygen, nitrogen and sulfur, preferably nitrogen. Halo includes bromo, chloro and fluoro.

Suitable examples of $R^1$ are recited below.

Alkyl includes $C_1$-$C_{10}$, preferably $C_1$14 $C_6$ alkyl, e.g. methyl, ethyl, n-propyl, isopropyl, n-butyl, isobutyl, n-pentyl, neopentyl, n-hexyl, octyl, decyl. Alkenyl includes $C_3$-$C_{10}$ alkenyl, e.g., allyl, isopropenyl, butenyl, pentenyl, hexenyl, octenyl, decenyl. Alkynyl includes $C_3$-$C_6$ alkynyl, e.g., propynyl, butynyl, hexynyl.

Cycloalkyl includes cyclo($C_3$-$C_7$)alkyl, e.g., cyclopropyl, cyclopentyl, cyclohexyl, cycloheptyl. Cycloalkylalkyl includes, e.g., cyclo($C_3$-$C_6$)alkyl($C_1$-$C_4$) alkyl, e.g., cyclopropylmethyl, cyclopropylethyl, cyclohexylmethyl, cyclohexylethyl.

Alkoxyalkyl includes ($C_1$-$C_6$)alkoxy($C_2$-$C_6$)alkyl, e.g., 2-methoxyethyl, 2-ethoxyethyl. Oxoalkyl includes oxo($C_3$-$C_6$)alkyl, e.g., 2-oxopropyl. Alkoxycarbonylalkyl includes ($C_1$-$C_6$)alkoxycarbonyl($C_1$-$C_4$)alkyl, methoxycarbonylmethyl, butoxycarbonylmethyl. Acyl includes, e.g., acetyl, propionyl, butyryl, hexanoyl, benzoyl.

Dialkylaminoalkyl includes di($C_1$-$C_6$) alkylamino ($C_2C_6$) alkyl, e.g., 2-(dimethylamino)ethyl, 2-(diethylamino) ethyl. Alkoxycarbonyl includes ($C_1C_6$)alkoxycarbonyl, e.g., methoxycarbonyl, isobutoxycarbonyl. Hydroxyalkyl includes hydroxy($C_2$-$C_6$)alkyl, e.g., 2-hydroxyethyl, 2-hydroxypropyl. Haloalkyl includes halo($C_2$-$C_6$)alkyl, e.g., 2-chloropropyl, 2-fluoroethyl, 2bromoethyl, 2-iodoethyl.

Cyanoalkyl includes cyano($C_1$-$C_4$)alkyl, e.g., cyanomethyl. Heteroarylalkyl includes heteroaryl ($C_1$-$C_4$)alkyl wherein the heteroaryl moiety is 5- to 7-membered rings containing 1-3nitrogen atoms, said heteroaryl moiety being optionally fused with a benzene ring, e.g., 2pyridylmethyl, 4,6-diamino-2-triazinylmethyl. Aryl includes e.g., phenyl, naphthyl. Heterocycloalkyl includes e.g., piperidinyl, pyrrolidinyl. Arylalkyl or substituted arylalkyl includes e.g., benzyl, phenethyl, p-methoxybenzyl, m-chlorobenzyl, o-nitrobenzyl, p-aminobenzyl, p-nitrobenzyl, p-tert-butylbenzyl, p-fluorobenzyl.

Suitable examples of alkyl in $R^2$ include $C_1$-$C_{10}$, preferably $C_1$-$C_6$ alkyl, e.g., methyl, ethyl, n-propyl, isopropyl, n-butyl, isobutyl, n-pentyl, neopentyl, n-hexyl.

Suitable examples of $R^3$ and $R^4$ are recited below.

Alkyl includes $C_1$-$C_{10}$, preferably $C_1$-$C_6$ alkyl, e.g., methyl, ethyl, n-propyl, isopropyl, n-butyl, isobutyl, n-pentyl, neopentyl, n-hexyl. Alkenyl includes $C_3$-$C_{10}$, preferably $C_3$-$C_8$ alkenyl, e.g., allyl, isopropenyl, butenyl, pentenyl, hexenyl, octenyl. Acyl includes, e.g., acetyl, propionyl, butyryl, hexanoyl, benzoyl. Alkoxyalkyl includes $(C_1-C_6)$alkoxy$(C_2-C_6)$alkyl, e.g., 2-methoxyethyl, 2-ethoxyethyl. Arylalkyl or substituted arylalkyl includes e.g., benzyl, phenethyl, p-methoxybenzyl, m-chlorobenzyl, o-nitrobenzyl, p-aminobenzyl, p-nitrobenzyl, p-tertbutylbenzyl, p-fluorobenzyl.

The pharmaceutically acceptable salts of the compounds of formula (I) include acid addition salts and quaternary ammonium salts. The acid addition salts refer to the compounds of formula (I) wherein a pharmaceutically acceptable organic or inorganic acid is added to a nitrogen atom at the 3- and/or 9-position of the azabicyclo ring. Those salts include hydrochloride, hydrobromide, hydroiodide, sulfate, phosphate, oxalate, maleate, fumarate, lactate, realate, citrate, tartrate, benzoate and methanesulfonate. The quaternary ammonium salts refer to the compounds of formula (I) which are quaternised at a nitrogen atom at the 3- and/or 9-position of the azabicyclo ring by a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p- toluenesulfonate.

The compounds of formula (I) and their pharmaceutically acceptable salts including acid addition salts and quaternary ammonium salts may form hydrates or solyates which are included within the scope of the invention.

Some of the compounds of formula (I) have chiral or prochiral centers, thus existing in the stereoisomeric forms. Those stereoisomer and mixtures thereof are also included within the scope of the invention.

The compounds of formula (I) can be prepared by a variety of processes based on known synthetic reaction. Basically, those compounds can be prepared through an amide coupling by reacting indazole-3-carboxylic acids of formula (II) or the acid amide forming reactive derivatives thereof

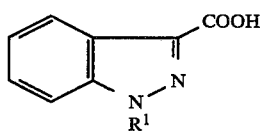

(II)

wherein $R^1$ has the same meaning as described above, with 3,9-diazabicyclo[3.3.1]nonan-7-amine derivatives of formula (III)

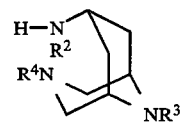

(III)

wherein $R^2$, $R^3$ and $R^4$ are as defined above. Suitable acid amide forming reactive derivatives include mixed acid anhydrides and acid halides.

Alternatively, the amide coupling may be carried out by reacting the compound of formula (III) with diindazolo[2,3-a,2',3'-d]pyrazine-7,14-dione (1H-indazole-3-carboxylic acid dimer) of formula (IV)

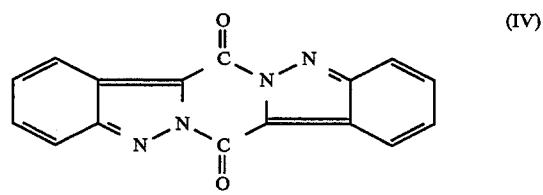

(IV)

Further, the compounds of the invent ion may be converted into other compounds of the invention in conventional manner, e.g., by converting one or more of the groups $R_1$, $R_2$, $R_3$ and $R_4$ in the reaction products prepared by the above reaction into the desired groups.

The compounds of formula (III) can be prepared, e.g., by the process disclosed in J. Org. Chem., 26, 395 (1961). Alternatively, they may be prepared by condensing N,N-bis (2,2-dimethoxyethyl) methylamine to form 7 -oxo-3,9-dimethyl-3,9-diazabicyclo[3.3.1]nonane, reacting said nonane with hydroxyamine to afford the corresponding oxime, followed by amination under catalytic reduction to give 3,9-dimethyl-3,9-diazabicyclo[3.3.1]nonan-7-amine. The diazabicyclo-nonanamine derivatives thus prepared are reacted with the amide forming reactive derivatives of the indazole carboxylic acids. The reaction mixtures are washed, extracted and purified to obtain the desired end product of the invention.

Giving an example of using the indazole carboxylic acid dimer as the amide forming reactive derivatives, a series of the reaction steps as mentioned above are shown in the following Reaction Scheme 1.

Reaction Scheme 1

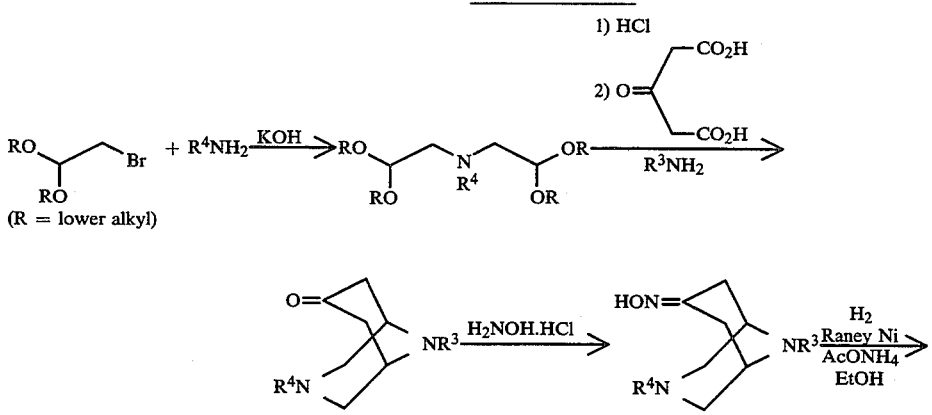

-continued
Reaction Scheme 1

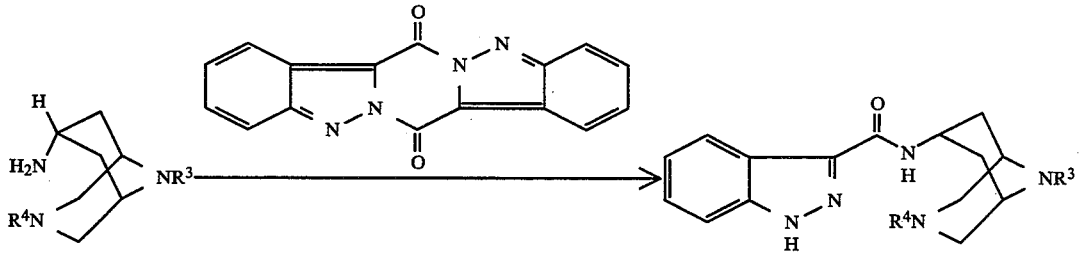

If an acid halide such as indazole-3-carboxylic acid chloride is for example used as the reactive derivatives of an indazole carboxylic acid represented by lo formula (II), the reaction with the compounds of formula (III) is carried out in a non-aqueous organic solvent at a temperature in the range of −80° C. to a boiling point of the solvent. If necessary, said reaction may be effected in the presence of an inorganic or organic acid binder. The organic solvents used include diethyl ether, diisopropyl ether, tetrahydrofuran, dimethoxyethane, 1,4-dioxane, dimethylformamide and dimethyl sulfoxide. The acid binders used include triethylamine, tri-n-butylamine, pyridine, dimethylaniline, tetramethyl urea, metallic magnesium, n-butyl lithium, lithium diisopropyl amide, sodium amide, sodium hydride and metallic sodium. Subsequently, the reaction mixtures are washed, extracted and purified to obtain the desired compounds of formula (I).

If desired, the substituents $R^1$–$R^4$ in the diazabicyclo derivatives prepared by amide coupling as mentioned above can be converted into other desired substituents in a conventional manner, depending on the reactivity of those substituents, easiness of the reaction operation or the like.

For instance, the amide reaction products of formula (I) ($R^1$, $R^2$=H) can be treated with alkyl halides e.g., methyl iodide or methoxy benzyl chloride, in the presence of a base, e.g., sodium hydride or n-butyl lithium, thus converting one or both of $R^1$ and $R^2$ into the desired alkyl group. The amide reaction products ($R^2$=H) can be treated with alkyl halides, e.g., methyl iodide in the presence of a base, e.g., n-butyl lithium, thus converting $R^2$ into the desired alkyl group.

Further, the amide reaction products ($R^1$=H) can be treated with acyl halides, e.g., acetyl chloride in the presence of a base, e.g., sodium hydride to convert $R^1$ into the desired acyl group. The above reaction is shown in the following Reaction Scheme 2.

Reaction Scheme 2

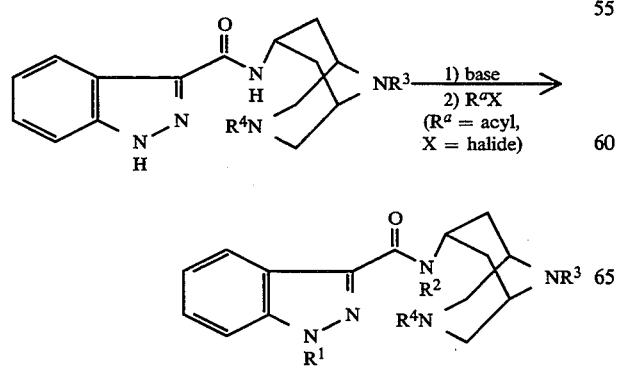

-continued
Reaction Scheme 2
($R^1 = R^a$, $R^2 = H$ or $R^1 = R^2 = R^a$)

The compounds of formula (I) wherein $R^3$ and/or $R^4$ is benzyl and other substituents are lower alkyl can be hydrogenated in the presence of a hydrogenation catalyst, e.g., palladium, thus converting benzyl group in $R^3$ and/or $R^4$ into hydrogen. This reaction is shown in the following Reaction Scheme 3.

Reaction Scheme 3

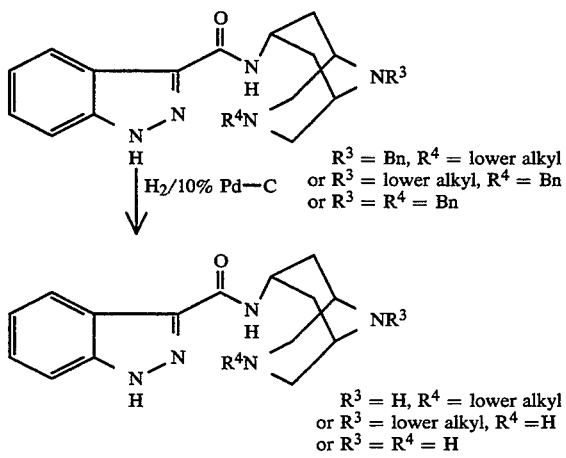

Likewise, the reduced reaction products wherein $R^3$ and/or $R^4$ is hydrogen are treated with alkyl halides, acyl halides or acid arthydrides in the presence of a base, thus converting $R^3$ and/or $R^4$ into the desired alkyl or acyl group. This reaction is shown in the following Reaction Scheme 4.

Reaction Scheme 4

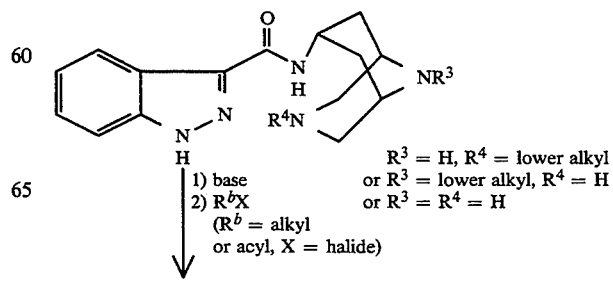

-continued
Reaction Scheme 4

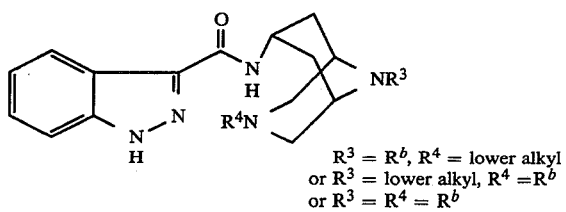

$R^3 = R^b$, $R^4$ = lower alkyl
or $R^3$ = lower alkyl, $R^4 = R^b$
or $R^3 = R^4 = R^b$ Similarly, the desired derivatives of formula (I) ($R^1$=hydroxyalkyl or $R^1$ =amino substituted phenyl) may be prepared by reduction of the corresponding compounds ($R^1$=carbonylalkyl or $R^1$=nitro substituted phenyl).

Likewise, the desired derivatives of formula (I) ($R^1$=4,6-diamino-2-triazinylmethyl) may be prepared by reacting the corresponding compounds ($R^1$=cyanomethyl ) with dicyandiamide.

The compounds of the invention may be isolated and purified in conventional manner.

Pharmaceutically acceptable salts of the compounds of formula (I) may be formed in conventional way. The acid addition salts may be formed for example by reaction of the base compound of formula (I) with a pharmaceutically acceptable inorganic acid such as hydrochloric, hydrobromic, hydroiodic, sulfuric and phosphoric acids or a pharmaceutically acceptable organic acid such as oxalic, maleic, fumaric, lactic, malic, citric, tartaric, benzoic and methanesulfonic acids. The quaternary ammonium salts may be formed in conventional way, e.g., by reaction of the compound of formula (I) with a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p-toluenesulfonate. The quaternization reaction can be effected in an organic solvent at a temperature in the range of −20° C. to a boiling point of the solvent. The organic solvents include diethyl ether, diisopropyl ether, tetrahydrofuran, dimethoxyethane, 1,4-dioxane, benzene, toluene, xylene, dimethylformamide and dimethyl sulfoxide. If a low boiling solvent such as diethyl ether or a low boiling reactant such as methyl chloride is used, the reaction is preferably carried out under pressure in a stainless closed tube. The reaction may be effected with no solvent.

Insofar as the preparation of any particular starting materials is not specifically described these are known or may be prepared in conventional manner.

The compounds of the present invention antagonize the action of 5-HT at 5-HT$_3$ receptors in the central nervous system and are useful in the treatment of psychotic disorders such as schizophrenia, mania, depression, anxiety, dementia, cognitive disorders and dependency on drugs as well as neurotic diseases such as migraine. The compounds of the invention antagonize the action of 5-HT at 5-HT$_3$ receptors in the peripheral nervous system and are useful in the treatment of gastric stasis symptoms of gastrointestinal dysfunction such as occur with dyspepsia, reflux oesophagitis, flatulence as well as gastrointestinal disorders such as gastritis, peptic ulcer, diarrhea occurred by various causes and Hirschsprung's disease. The present compounds are also in the treatment of nausea and vomiting, particularly that associated with cancer chemotherapy and radiotherapy.

The invention provides in another aspect a pharmaceutical composition having a selective antagonism of 5-HT at 5-HT$_3$ receptors, which comprises as an active ingredient an effective amount of a compound of formula (I), or a pharmaceutically acceptable salt thereof. Such compositions may be formulated in conventional manner using one or more pharmaceutically acceptable carriers and/or excipients.

The compounds of the invent ion can usually be administered orally or parenterally in the form of a pharmaceutical formulation. The pharmaceutical formulation includes tablets, capsules, suppositories, troches, syrups, creams, ointments, plasters, cataplasms, granules, powders, injections, suspensions and the like. It may be in bilayered or multilayered tablet with other drugs. The tablets may also be coated with a conventional coating to form, e.g., sugar-coated, enteric-coated or film-coated tablets.

In preparing solid formulations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, glycerin, polyethylene glycol, stearic acid, magnesium stearate and talc are employed.

A vegetable or synthetic wax or fat or a similar base is used in preparing the semi-solid formulations.

As additives in preparing the liquid formulations are used, for example, sodium chloride, sorbitol, glycerin, olive oil, almond oil, propylene glycol and ethyl alcohol.

The active ingredient is contained in the formulation in an amount of 0.001–100% by weight, suitably 0.01–50% by weight in the case of formulations for oral administration and 0.001–10% by weight in the case of formulations for injection based on the weight of the formulations.

Route and dosage of administration for the compounds of the invention are not specifically limited and are appropriately chosen depending upon form of the formulation, age and sex of the patient, severity of the disease and other factors. Daily dosage of the active ingredient is 0.01–1000 mg.

The following examples illustrate the invention.

EXAMPLE 1 endo-3,9-Dimethyl-3,9-diazabicyclo[3.3.1]non-7-yl lally 1 indazole -3-carboxamide

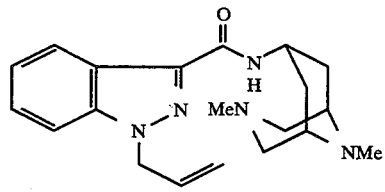

endo-3,9-Dimethyl-3,9-diazabicyclo[3.3.1]non-7-yl 1H-indazole-3-carboxamide (1.00 g ) was dissolved in DMF (30 ml), then 60% sodium hydride (0.153 g) add and the mixture was stirred for 30 minutes. Allyl bromide (0.463 g) was added at room temperature and stirred for 10 hrs. The reaction solution was poured into water (300 ml) and extracted with ethyl acetate (3×100 ml). The organic layer was washed with saturated saline solution, dried over anhydrous magnesium sulfate and concentrated under reduced pressure to afford a crude product (1.03 g). Recrystallization from ethanol gave the title compound (0.52 g).

m.p. 163°–164° C.

1 H NMR (CDCl3) δ1.48 (d, J=15 Hz, 2H), 2.45 (s, 3H), 2.53 (s, 3H), 2.47–2.51 (m, 2H), 2.56–2.60 (m, 2H), 2.72(d, J=11 Hz, 2H), 2.87 (bs, 2H), 4.62 (td, J=7, 10Hz, 1H), 4.99 (td, J=2, 5 Hz, 2H), 5.16 (dd, J=2, 17 Hz, 1H), 5.24 (dd, J=1, 10 Hz, 1H), 6.03 (ddd, J=5, 10, 17 Hz, 1H), 7.20–7.29 (m, 1H), 7.36–7.40 (m, 2H), 8.42 (d, J=8 Hz, 1H), 11.22 (d, J=10 Hz, 1H) IR (KBr) 2826, 2798, 1650, 1519, 1489, 1373, 1263, 1189, 788, 742 cm$^{-1}$

EXAMPLE 2 endo-3,9-Dimethyl-3,9-diazabicyclo[3.3.1]non-7-yl 1-allylindazole-3-carboxamide hydrochloride The compound prepared in Example 1 (0.50 g) was dissolved in a mixed solution of ethyl acetate (10 ml) and chloroform (3 ml) and 4N hydrochloric acid/ethyl acetate solution (1 ml) was added at room temperature. The precipitated crystals were filtered off and dried under reduced pressure to afford the title compound (0.60 g). m.p. 129°–130° C.

EXAMPLE 3 endo-3,9-Dimethyl-3,9-diazabicyclo[3.3.1]non-7-yl 1-cyclohexylmethylindazole-3-carboxamide

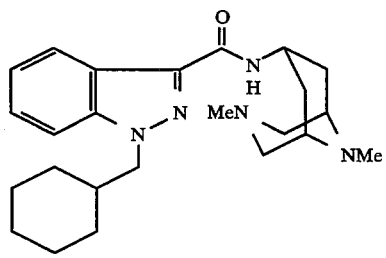

Following the procedure outlined in Example 1, the title compound was prepared by reacting endo-3,9-dimethyl-3, 9-diazabicyclo[3.3.1]non-7-yl 1H-indazole-3-carboxamide with cyclohexylmethyl bromide and recrystallization from hexane/ethyl acetate.

m.p. 155°–156° C.

$^1$H NMR (CDCl3) δ0.98–1.07 (m. 2H), 1.16–1.21 (m. 3H), 1.50 (d, J=15H z, 2H), 1.60–1.73 (m. 5H), 1.94–2.04 (m, 1H), 2.48 (s, 3H), 2.54 (s, 3H) 2.45–2.51 (m, 2H), 2.59 (dd, J=3, 11 Hz, 2H), 2.74 (d, J=11 Hz, 2H), 2.8 8 (bs. 2H), 4.18 (d, J=7 Hz, 2H), 4.64 (td, if=7, 10Hz, 1H), 7.20–7.25 (m, 1H), 7.35–7.39 (m, 2H), 8.41 (d, J=8 Hz, 1H), 11.09 (d, J=10 Hz, 1H) IR (KBr) 2924, 2844, 2802, 1650, 1525, 1489, 1451, 1335, 1274, 1217, 1177, 794, 751 cm$^{-1}$

Further, the title compound was converted to the hydrochloride, following the procedure outlined in Example 2. m.p. 152°–154° C.

EXAMPLE 4 endo-3,9-Dimethyl-3,9-diazabicyclo'3.3.1]non-7-yl 1-cycylopropylmethylindazole3-carboxamide

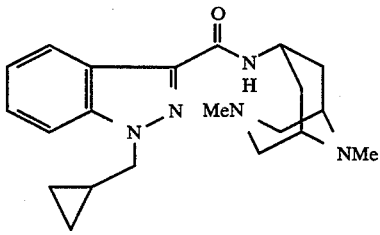

Following the procedure outlined in Example 1, the title compound was prepared by reacting endo-3,9-dimethyl-3,9-diazabicyclo [3.3.1]non-7-yl 1H-indazole-3-carboxamide with cyclopropylmethyl bromide and recrystallization from hexane/ethyl acetate.

m.p. 136°–137° C.

$^1$H NMR (CDCl3) δ0.40(m, 2H), 0.59 (m, 2H), 1.36 (m, 1H), 1.50 (d, J=15 Hz, 2H), 2.44–2.51 (m, 2H), 2.48 (s, 3H), 2.53 (s, 3H), 2.59 (dd, J=3, 11 Hz, 2H), 2.73 (d, J=11 Hz, 2H), 2.87 (bs, 2H), 4.26 (d, J=7 Hz, 2H), 4.64 (td, g=7, 11 Hz. 1H), 7.20–7.25 (m, 1H), 7.35–7.39 (m, 2H), 8.42 (d, J=8 Hz, 1H), 11.13 (d, g=11 Hz, 1H)

IR (KBr) 2926, 2798, 1642, 1516, 1491, 1372, 1335, 1266, 1205, 1165, 1132, 794, 782, 760 cm$^{-1}$

Further, the title compound was converted to the hydrochloride, following the procedure outlined in Example 2. m.p. 235°–237° C. (dec.)

EXAMPLE 5 endo-3,9-Dimethyl-3,9-diazabicyclo[3.3.13non-7-yl 1-(4-methoxybenzyl) indazole-3-carboxamide

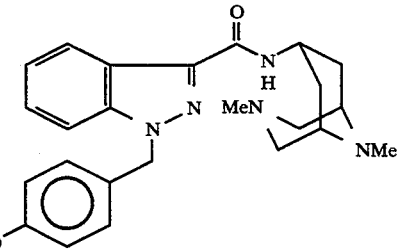

Following the procedure outlined in Example 1, the title compound was prepared by reacting endo-3,9-dimethyl-3,9-diazabicyclo[3.3.1]non-7-yl 1H-indazole-3-carboxamide with 4-methoxybenzyl chloride and purification by silica gel column chromatography (20/1/0.05 chloroform/methanol/ammonia water).

Foamy solid $^1$H NMR (CDCl3) δ1.46 (d, J=15 Hz, 2H), 2.35 (s, 3H), 2.41–2.48 (m, 2H), 2.48 (s, 3H), 2.54 (d, J=11 Hz, 2H), 2.67 (d, J=11 Hz, 2H), 2.81 (bs, 2H), 3.71 (s, 3H), 4.59–4.65 (m, 1H), 5.48 (s, 2H), 6.79–6.80 (m, 2H), 7.10–7.12 (m, 2H), 7.18–7.24 (m, 1H), 7.27–7.33 (m, 2H), 8.43–8.45 (m, 1H) 11.23 (d, J=11 Hz. 1H)

IR (KBr) 2930, 2836, 2802, 1650, 1614, 1515, 1489, 1247, 1175, 1030, 789, 705 cm$^{-1}$

Further, the title compound was converted to the hydrochloride, following the procedure outlined in Example 2. m.p. 152°–154° C.

EXAMPLE 6 endo-3,9-Dimethyl-3,9-diazabicyclo[3.3.1]non-7-yl 1-(7octenyl) indazole-3-carboxamide

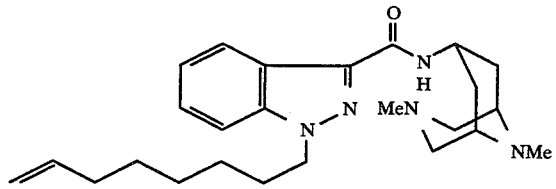

Following the procedure outlined in Example 1, the title compound was prepared by reacting endo-3,9-dimethyl-3,9-diazabicyclo [3.3.1]non-7-yl 1H-indazole-3-carboxamide with 8-bromo-1-octene and purification by silica gel column chromatography (20/1/0.05 chloroform/methanol/ammonia water). Pale yellow oil $^1$H NMR (CDCl$_3$) δ1.26–1.35 (m, 6H), 1.49 (d, J=15 Hz, 2H), 1.91–2.02 (m, 4H), 2.44–2.50 (m, 2t), 2.48 (s, 3H), 2.53 (s, 3H), 2.56–2.60 (m, 2H), 2.72 (d, J=11 Hz, 2H), 2.86 (bs, 2H), 4.33–4.36 (m, 2H), 4.64 (td, J=7, 10 Hz, 1H), 4.92 (dd, J=2, 10 Hz, 1H), 4.97 (dd, J=1, 17 Hz, 1H), 5.77 (dd d, J=7, 10, 17 Hz, 1H), 7.21–7.25 (m, 1H), 7.34–7.39 (m, 2H), 8.42 (d, J=8 Hz, 1H), 11.11 (d, g=10 Hz, 1H)

IR (neat) 2932, 2853, 2802, 1648, 1528, 1493, 1464, 1376, 1271, 1218, 1178, 796, 753 cm$^{-1}$ Further, the title compound was converted to the hydrochloride, following the procedure outlined in Example 2. m.p. 114°–116° C.

EXAMPLE 7 endo-3,9-Dimethyl-3,9-diazabicyclo[3.3–1]non-7-Yl 1-(2propynyl) indazole-3-carboxamide

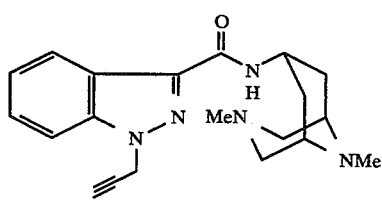

Following the procedure outlined in Example 1, the title compound was prepared by reacting endo-3,9-dimethyl-3,9-diazabicyclo [3.3.1]non-7-yl 1H-indazole-3-carboxamide with propargyl chloride. $^1$H NMR (CDCl$_3$) 67 1.47 (d, J=15 Hz, 2H), 1.92 (bs, 1H), 2.49 (s, 3H), 2.53 (s, 3H), 2.45–2.51 (m, 2H), 2.56–2.60 (m, 2H), 2.72 (d, J=11 Hz, 2H), 2.87 (bs, 2H), 4.59–4.65 (m, 1H), 5.73 (d, J=6 Hz, 2H), 7.28–7.32 (m, 1H), 7.39–7.44 (m, 1H), 7.77 (d, J=8 Hz, 1H), 8.45 (d, J=8 Hz, 1H, 11.28 (d J=10 Hz, 1H)

IR (KBr) 2934, 2810, 1658, 1535, 1497, 1340, 1273, 1184, 799, 758 cm$^{-1}$

Further, the title compound was converted to the hydrochloride, following the procedure outlined in Example 2. m.p. 216°–220° C.

EXAMPLE 8 endo-3,9-Dimethyl-3,9-diazabicyclo[3.3.1]non-7-yl 1-(3-methyl-2-butenyl) indazole-3-carboxamide

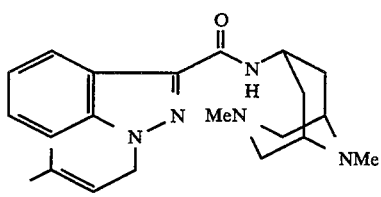

Following the procedure outlined in Example 1, the title compound was prepared by reacting endo-3,9-dimethyl-3,9-diazabicyclo [3.3.1]non-7-yl 1H-indazole-3-carboxamide with isoprenyl bromide.

$^1$H NMI (CDCl$_3$) δ1.48 (d, J=15 Hz, 2H), 1.75 (s, 3H), 1.78 (s, 3H), 2.43–2.52 (m, 2H), 2.47 (s, 3H), 2.53 (s, 3H), 2.57 (dd, J=3, 11 Hz, 2H), 2.73 (d, J=11 Hz, 2H), 2.86 (bs. 2H), 4.61–4.65 (m, 1H), 4.99 (d, J=7 Hz, 2 H), 5.41 (m, 1H), 7.21–7.25 (m, 1H), 7.37 (d, J=4 Hz, 2H), 8.42 (d, J=8 Hz 1H), 11.16 (d, J=11 Hz, 1H)

IR (KBr) 2930, 2805, 1652, 1530, 1522, 1493, 1265, 1178, 753 cm$^{-1}$

Further, the title compound was converted to the hydrochloride, following the procedure outlined in Example 2. m.p. 133°–135° C./180° C./210° C. (dec.)

EXAMPLE 9 endo-3,9-Dimethyl-3,9-diazabicyclo[3.3.1]non-7-yl 1-(4nitrobenzyl) indazole-3-carboxamide

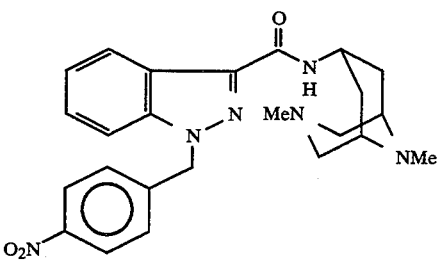

Following the procedure outlined in Example 1, the title compound was prepared by reacting endo-3,9-dimethyl3,9-diazabicyclo [3.3.1]non-7-yl 1H-indazole-3-carboxamide with 4-nitrobenzyl chloride and purification by silica gel column chromatography (30/1/0.05 chloroform/methanol/ammonia water). Yellow oil $^1$H NMR (CDCl$_3$) δ1.48 (d. J=15 Hz, 2H), 2.27 (s, 3H), 2.43–2.56 (m, 4H), 2.53 (s, 3H), 2.66 (d, J=11 Hz, 2H), 2.86 (bs, 2H), 4.63 (td, J=7, 10Hz, 1H), 5.68(s, 2H), 7.26–7.29 (m, 4H), 7.37 (d, J=8 Hz, 2H), 8.15 (d, J=9 Hz 2H), 8.46 (d, J=8 Hz, 1H), 11.11 (d. J=11 Hz, 1H)

IR (neat) 2939, 2812, 1649, 1532, 1497, 1351, 1263, 1221, 1180, 864, 794, 760 cm$^{-1}$ Further, the title compound was converted to the hydrochloride, following the procedure outlined in Example 2. m.p. 166°–168° C. (dec.)

EXAMPLE 10 endo-3,9-Dimethyl-3,9-diazabicyclo[3.3.1]non-7-yl 1-cyanomethylindazole-3-carboxamide

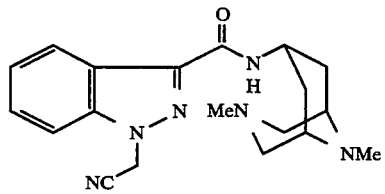

Following the procedure outlined in Example 1, the title compound was prepared by reacting endo-3,9-dimethyl-3,9-diazabicyclo [3.3.1]non-7-yl 1H-indazole-3-carboxamide with bromoacetonitrile and purification by silica gel column chromatography (10/1/0.05 chloroform/methanol/ammonia water).
m.p. 201°–202° C. (recrystallized from hexane/ethyl acetate)

$^1$H NMR (CDCl$_3$) δ1.47 (d, J=15 Hz, 2H), 2.45–2.54 (m, 2H), 2.51 (s, 3H), 2.54 (s, 3H), 2.59–2.62 (m, 2H), 2.72 (d, J=11 Hz, 2}t), 2.88 (bs, 2H), 4.61 (td, J=7, 10 Hz, 2H), 5.27 (s, 2H), 7.33–7.37 (m, 1H), 7.44 (d, J=8 Hz, 1H), 7.50–7.54 (m, 1H), 8.47 (d, J=8 Hz, 1H), 11.37 (d, J=10 Hz, 1H)

IR (KBr) 2938, 2840, 2798, 1640, 1525, 1491, 1467, 1413, 1372, 1261, 1184, 1132, 785, 757 cm$^{-1}$

Further, the title compound was converted to the hydrochloride, following the procedure outlined in Example 2. m.p. 157°–159° C. (dec.)

EXAMPLE 11 endo-3,9-Dimethyl-3,9-diazabicyclo[3.3.1]non-7-yl 1-(4-tert-butylbenzyl) indazole-3-carboxamide

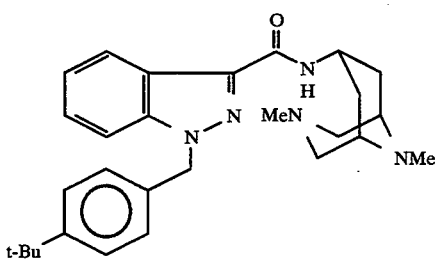

Following the procedure outlined in Example 1, the title compound was prepared by reacting endo-3,9-dimethyl-3,9-diazabicyclo [3.3.1]non-7-yl 1H-indazole-3-with 4-tert-butylbenzyl bromide and purification by silica gel column chromatography (20/1/0.05 chloroform/methanol/ammonia water). Pale yellow oil $^1$H NMR (CDCl$_3$) δ1.28 (s, 9H), 1.48 (d, J=15 Hz, 2H), 2.30 (s, 3H), 2.43–2.50 (m, 2H), 2.52 (s, 3H), 2.54–2.69 (m, 2H), 2.86 (d, J=7 Hz, 2H), 2.92 (bs, 2H), 4.63 (td, J=7, 10 Hz, 1H), 5.54 (s, 2H), 7.12 (d, J=8 Hz, 2H), 7.21–7.25 (m, 1H), 7.31 (d, J=8 Hz. 2H), 7.33–7.34 (m, 2H), 8.43 (d, J=8 Hz, 1H), 11.20 (d, J=11 Hz, 1H)

IR (neat) 2970, 2932, 2810, 1648, 1529, 1494, 1276, 1263, 1180, 914, 795, 755, 738 cm$^{-1}$ Further, the title compound was converted to the hydrochloride, following the procedure outlined in Example 2. m.p. 171°–173° C.

EXAMPLE 12 endo-3,9-Dimethyl-3,9-diazabicyclo[3.3.1]non-7-yl 1-(2-oxopropyl) indazole-3-carboxamide

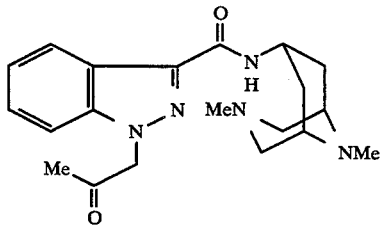

Following the procedure outlined in Example 1, the title compound was prepared by reacting endo-3, 9-dimethyl-3,9-diazabicyclo [3.3.1]non-7-yl 1H-indazole-3-carboxamide with chloroacetone and recrystallization from hexane/ethyl acetate.
m.p. 230°–232° C.

$^1$H NMR (CDCl$_3$) δ1.48 (d, J=15 Hz, 2H), 2.05 (s, 3H), 2.39 (s, 3H), 2.42–2.51 (m, 2H), 2.53 (s, 3H), 2.57 (dd, J=3, 11 Hz, 2H), 2.69 (d, J=11 Hz 2H), 2.87 (bs, 2H), 4.62 (td, J=7, 10 Hz, 1H), 5.08 (s, 2H), 7.26–7.32 (m, 2H), 7.42–7.46 (m, 1H), 8.47 (d, J=8 Hz, 1H), 11.26 (d, J=10 Hz, 1H) IR (KBr) 2920, 2832, 1737, 1649, 1644, 1525, 1492, 1373, 1314, 1268, 1173, 791, 743cm$^{-1}$

Further, the title compound was converted to the hydrochloride, following the procedure outlined in Example 2. m.p. 169°–171° C.

EXAMPLE 13 endo-3,9-Dimethyl-3,9-diazabicyclo[3.3.1]non-7-yl 1-(3-chlorobenzyl)indazole-3-carboxamide

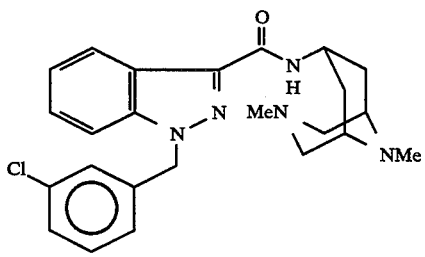

Following the procedure outlined in Example 1, the title compound was prepared by reacting endo-3,9-dimethyl-3,9-diazabicyclo[3.3.1]non-7-yl 1H-indazole-3-carboxamide with chlorobenzyl chloride and purification by silica gel column chromatography (10/1/0.05 chloroform/methanol/ammonia water ). m.p. 159°–161° C. (recrystallized from hexane/ethyl acetate)

$^1$H NMR (CDCl$_3$) δ1.48 (d, J=15 Hz, 2H), 2.29 (s, 3H), 2.53 (s, 3H), 2. 44–2.56 (m, 4H), 2.68 (d, J=11 Hz, 2H), 2.86 (bs, 2H), 4.63 (td, J=7, 10 Hz, 1H), 5.54 (s, 2H), 7.03 (d, J=7 Hz, 1H ), 7.18 (s, 1H), 7.19–7.40 (m, 5H), 8.45 (d, J=8Hz, 1H), 11.19 (d, J=11 Hz, 1H)

IR (KBr) 2924, 2802, 1646, 1617, 1521, 1475, 1252, 1215, 1174, 1085, 783, 753 cm$^{-1}$

Further, the title compound was converted to the hydrochloride, following the procedure outlined in Example 2. m.p. 141°–143 ° C.

EXAMPLE 14 endo-3,9-Dimethyl-3,9-diazabicyclo[3.3.1]non-7-yl 1-(2-nitrobenzyl) indazole-3-carboxamide

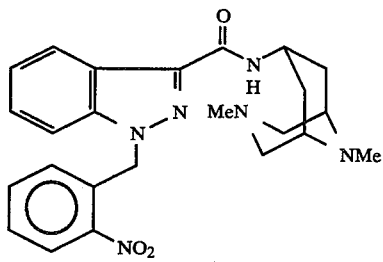

Following the procedure outlined in Example 1, the title compound was prepared by reacting endo-3,9-dimethyl-3,9-diazabicyclo[3.3.1]non-7-yl 1H-indazole-3-carboxamide with 2-nitrobenzyl chloride and purification by silica gel column chromatography (20/1/0.05 chloroform/methanol/ammonia water).

m.p. 174°–175° C. (recrystallized from hexane/ethyl acetate)

$^1$H NMR (CDCl$_3$) δ1.48 (d, J=15 Hz, 2H), 2.17 (s, 3H), 2.51 (s, 3H), 2.43–2.53 (m, 4H), 2.63 (d, J=11 Hz, 2H), 2.84 (bs, 2H), 4.62 (td, J=7, 10 Hz, 1H), 6.01 (s, 2), 6.52 (m, 1H), 7.29–7.32 (m, 2H), 7.38–7.47 (m, 3H) 8.17–8.19 (m, 1H), 8.49 (d, J=8 Hz, 1H), 11.26 (d, J=10 Hz, 1H)

IR (KBr) 2916, 2802, 1645, 1608, 1533, 1489, 1337, 1269, 1186, 1177, 1134, 862, 787, 749, 727 cm$^{-1}$

Further, the title compound was converted to the hydrochloride, following the procedure outlined in Example 2. m.p. 154°–156° C.

EXAMPLE 15 endo-3,9-Dimethyl-3,9-diazabicyclo[3.3.1]non-7-yl 1-(2-pyridylmethyl) indazole-3-carboxamide

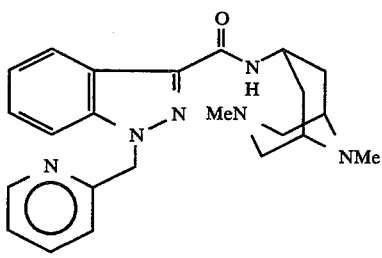

Following the procedure outlined in Example 1, the title compound was prepared by reacting endo-3,9-dimethyl-3,9-diazabicyclo[3.3.1]non-7-yl 1H-indazole-3carboxamide with 2-chloromethylpyridine and purification by silica gel column chromatography (20/1/0.05 chloroform/methanol/ammonia water).

m.p. 106°–108° C. (recrystallized from hexane/ethyl acetate)

$^1$H NMR (CDCl$_3$) δ 1.48 (d, J=15 Hz, 2H), 2.29 (s, 3H), 2.44–2.55 (m, 4H), 2.52 (s, 3H), 2.67 (d, J=11 Hz, 2H), 2.85 (bs, 2H), 4.62 (td, J=7, 10 Hz, 1H), 5.72 (s, 2H), 6.60 (d, J=8 Hz, 1H) 7.18–7.22 (m, 1H, 7.24–7.29 (m, 1H), 7.35–7.39 (m, 2H), 7.54–7.58 (m, 1H), 8.45 (d, J=8 Hz, 1H), 8.60 (d, J=4 Hz. 1H), 11.28 (d, J=10 Hz, 1H)

IR (KBr) 3042, 2908, 2824, 1645, 1635, 1599, 1539, 1516, 1507, 1477, 1436, 1312, 1262, 1183, 958, 905, 788, 736 cm$^{-1}$

Further, the title compound was converted to the hydrochloride, following the procedure outlined in Example 2. m.p. 152°–154° C.

EXAMPLE 16 endo-3,9-Dimethyl-3,9-diazabicyclo[3.3.1]non-7-yl 1-methoxycarbonylmethylindazole-3-carboxamide

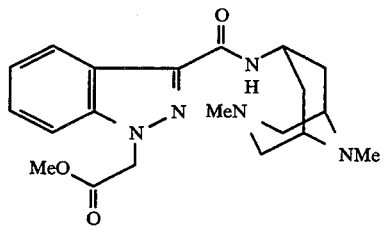

Following the procedure outlined in Example 1, the title compound was prepared by reacting endo-3,9-dimethyl-3,9-diazabicyclo[3.3.1]non-7-yl 1H-indazole-3-carboxamide with methoxy acetyl chloride and recrystallization from hexane/ethyl acetate.

m.p. 149°–151° C.

$^1$H NMR (CDCl$_3$) δ1.46 (d, J=15 Hz, 2H), 2.41 (s, 3H), 2.40–2.53 (m, 2H) 2.53 (s, 3H), 2.57 (dd, J=3, 11 Hz, 2H), 2.71 (d, J=11 Hz, 2H), 2.86 (bs, 2H), 3.76 (s, 3H), 4.61 (td, J=3, 10 Hz, 1H), 5.13 (s, 2H), 7.27–7.33 (m, 2H ), 7.41–7.45 (m. 1H), 8.44 (d, J=8 Hz, 1H), 11.27 (d, J=11 Hz, 1H)

IR (KBr) 2916, 2802, 1708, 1651, 1510, 1489, 1266, 1208, 1182, 905, 788, 746 cm$^{-1}$

Further, the title compound was converted to the hydrochloride, following the procedure outlined in Example 2. m.p. 154°–156° C.

EXAMPLE 17 endo-3,9-Dimethyl-3,9-diazabicyclo[3.3.1]non-7-yl 1-ethoxyethylindazole-3-carboxamide

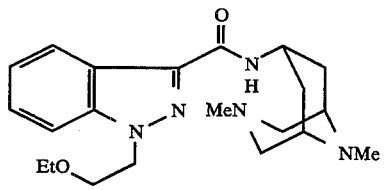

Following the procedure outlined in Example 1, the title compound was prepared by reacting endo-3,9-dimethyl-3,9-diazabicyclo[3.3.1]non-7-yl 1H-indazole-3-carboxamide with ethoxyethyl bromide and purification by silica gel column chromatography (15/1/0.05 chloroform/methanol/ammonia water).

Pale yellow oil $^1$H NMR (CDCl$_3$) δ1.10 (t, J=7 Hz, 3H), 1.48 (d, J=15 Hz, 2H), 2.48 (s, 3H), 2.44–2.50 (m, 2H), 2.53 (s, 3H), 2.57–2.61 (m, 2H), 2.72 (d, J=11 Hz, 2H), 2.87 (bs, 2H), 3.42 (q, J=7 Hz, 2H), 3.85 (t, J=6 Hz, 2H), 4.53 (t, J=6 Hz, 2H), 4.63 (td, J=7, 10 Hz, 1H), 7.22–7.26 (m, 1H), 7.36–7.40 (m, 1H), 7.48 (d. J=8 Hz, 1H), 8.40 (d, J=8 Hz, 1H), 11.16 (d, J=11 Hz, 1H) IR (neat) 2974, 2928, 2800, 1676. 1651, 1526, 1492, 1373, 1268, 1189, 1128, 795, 753 cm$^{-1}$ Further, the title compound was converted to the hydrochloride, following the procedure outlined in Example 2. m.p. 190°–193° C.

EXAMPLE 18 endo-3,9-Dimethyl-3,9-diazabicyclo[3.3.1]non-7-yl 1-isobutoxycarbonylindazole-3-carboxamide

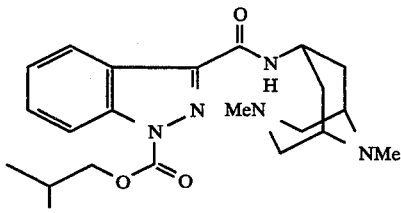

endo-3,9-Dimethyl-3,9-diazabicyclo (3.3.1]non-7-yl 1H-indazole-3-carboxamide (1.00 g) was dissolved in DMF (30 ml), triethylamine (0.3 g ) and 4-dimethylaminopyridine (0.15 g) were added and the mixture was stirred under ice-cooling for 30 minutes. Then isobutylchloroformate (0.51 g ) was added and the mixture was stirred at room temperature for 18 hrs. The reaction solution was poured into water (300 ml) and extracted with ethyl acetate (3×150 ml ). The organic layer was washed with saturated saline solution, dried over anhydrous magnesium sulfate and concentrated under reduced pressure to afford a crude product (0.87 g ). Purification by silica gel column chromatography (15/1/0.05 chloroform/methanol/ammonia water) gave the title compound (0.48 g).
Pale yellow oil $^1$H NMR(CDCl$_3$) δ1.07 (d, J=7 Hz, 6H), 1.48 (d, J=15 Hz, 2H), 2.19 (sep, J=7 Hz, 1H), 2.44–2.50 (m, 2H), 2.52 (s, 3H), 2.53 (s, 3H), 2.59 (dd, J=3 Hz, 2H), 2.73 (d, J=11 Hz, 2H), 2.88 (bs. 2H), 4.30 (d, J=7 Hz, 2H), 4.63
(td, J=7, 10 Hz, 1H), 7.39–7.43 (m, 1H), 7.53–7.58 (m, 1H), 8.19 (d, J=9 Hz, 1H), 8.59 (d, J=8 Hz, 1H), 11.60 (d, J=10Hz, 1H)

IR (neat) 2937, 2815, 2250, 1772, 1750, 1662, 1533, 1364, 1341, 1218, 1077, 760, 739 cm$^{-1}$ Further, the title compound was converted to the hydrochloride, following the procedure outlined in Example 2. m.p. 235°–237° C.

EXAMPLE 19 endo-3,9-Dimethyl-3,9-diazabicyclo[3.3.1]non-7-yl 1-(2hydroxypropyl) indazole-3-carboxamide

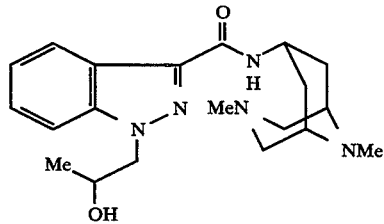

The product (2.00 g) of Example 12 was dissolved in a mixed solution of methanol (40 ml) and chloroform (10 ml) and then sodium borohydride (0.215 g) was added under ice-cooling. The mixture was stirred under ice-cooling for 14 minutes and at room temperature for 14 hrs. and the solvent was distilled off. The residue was dissolved in chloroform (50 ml) and washed with aqueous saturated sodium bicarbonate solution and then saturated saline solution. The organic layer was dried over magnesium sulfate and concentrated under reduced pressure to afford a crude product (2.72 g ). Purification by silica gel column chromatography (10/1/0.05 chloroform/methanol/ammonia water) gave the title compound (1. 52 g ).
m.p. 179°–180° C.

$^1$H NMR (CDCl$_3$) δ1.27 (d, J=5 Hz, 3H), 1.44 (d, J=15 Hz, 2H), 2.40–2.49 (m, 2H), 2.44 (s, 3H), 2.49 (s, 3H), 2.54 (dd, J=3, 11 Hz, 2H), 2.67 (d, J=11 Hz, 2H), 2.82 (bs, 2H), 3.22 (bs, 1H), 4.27–4.40 (m, 3H), 4.57–4.63 (m, 1H), 7.23–7.26 (m. 1H), 7.37–7.41 (m, 1H), 7.44 (d, J=8 Hz, 1H), 8.4 0 (d, J=8 Hz. 1H), 11.09 (d. J=10 Hz, 1H)

IR (neat) 3336, 2932, 2800, 1629, 1527, 1488, 1372, 1265, 1194, 1128, 958, 787, 742 cm$^{-1}$ Further, the title compound was converted to the hydrochloride, following the procedure outlined in Example 2. m.p. 157°–159° C.

EXAMPLE 20 endo-3,9-Dimethyl-3,9-diazabicyclo[3.3.1]non-7-yl 1-(4aminobenzyl) indazole-3-carboxamide

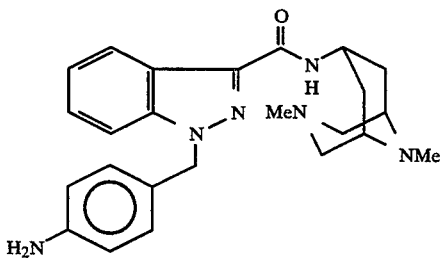

The product (0. 50 g ) of Example 9 was dissolved in a mixed solution of ethanol (4 ml) and concentrated hydrochloric acid (6 ml ) and then an ethanol solution (5 ml ) of stannous chloride dihydrate (2.16 g ) was added under ice-cooling. The mixture was stirred under ice-cooling for 30 minutes and at room temperature for 2 hrs. and then allowed to stand overnight. The precipitated crystals were filtered off, washed with ethanol and dried under reduced pressure. The residue was dissolved in water (30 ml ) and made strongly alkaline with sodium hydroxide. The water layer was extracted with chloroform. The organic layer was dried over potassium carbonate and concentrated under reduced pressure to afford brown oil (0.39 g). Purification by silica gel column chromatography (10/1/0.05 chloroform/methanol/ammonia water ) gave the title compound (0. 14 g ).
m.p. 186°–187° C. (recrystallized from ethyl acetate)

$^1$H NMR (CDCl$_3$) δ1.48 (d, J=15Hz, 2H), 2.37 (s, 3H), 2.43–2.58 (m, 4H), 2.53 (s, 3H), 2.70 (d, J=11Hz, 2H), 2.86 (bs, 2H), 3.66 (bs, 2H), 4.60–4.66 (m, 1H), 5.46 (s, 2H), 6.60 (d, J=8H, 2H), 7.00 (d, J=8 Hz, 2H), 7.20–7.24 (m, 1H), 7.30–7.40 (m, 2H), 8.41 (d, J=8 Hz, 1H), 11.19 (d, J=1 0 Hz, 1H)

IR (neat) 3410, 3156, 2932, 2804, 1649, 1638, 1619, 1525, 1510, 1485, 1312, 1176, 797, 749 cm$^{-1}$ Further, the title compound was converted to the hydrochloride, following the procedure outlined in Example 2. m.p. 180°–183° C. (dec.)

EXAMPLE 21 endo-3,9-Dimethyl-3,9-diazabicyclo[3.3.1]non-7-yl 1-(4,6diamino-2-triazinylmethyl)indazole-3-carboxamide

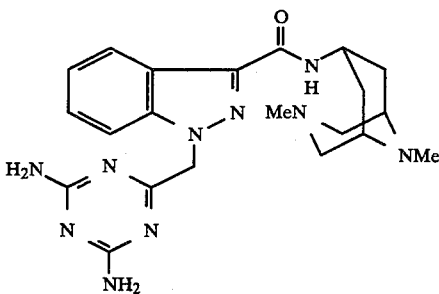

The product (0.58 g) of Example 10 and dicyandiamide (0.18 g) were dissolved in ethyleneglycol monomethyl ether (15 ml) and then 0.2 N potassium hydroxide ethyleneglycol monomethyl ether solution (1 ml) was added. The mixture was stirred at 90° C. for 5 hrs. and the precipitated crystals were filtered off and washed with hot water to afford the title compound (0.38 g).

m.p. >300° C.

$^1$H NMR (d-DMSO) δ1.27 (d, J=15 Hz, 2H), 2.21 (s, 3H), 2.30–2.56 (m, 6 H), 2.38 (s, 3H), 2.74 (bs, 2H), 4.33–4.38 (m, 1H), 5.35 (s, 2H), 6.60 bs, 4H), 7.23 (t, J=7 Hz, 1H), 7.38–7.42 (m, 1H), 7.67 (d, J=8 Hz, 1H), 8.18 (d, J=8 Hz, 1H), 11.19 (d, J=10 Hz, 1H)

IR (KBr) 3312, 3118, 2934, 2900, 2798, 1647, 1610, 1538, 1532, 1463, 1318, 1227, 1181, 797, 749 cm$^{-1}$

Further, the title compound was converted to the hydrochloride, following the procedure outlined in Example 2. m.p. 211°–215° C.

EXAMPLE 22 endo-3-Benzyl-9-methyl-3,9-diazabicyclo[3.3.1]non-7-yl 1H-indazole-3-carboxamide

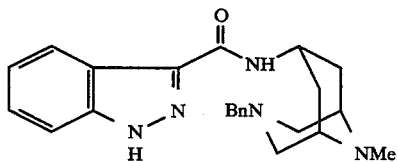

i) Preparation of N,N-bis (2,2-dimethoxyethyl) benzylamine

A mixture of bromoacetaldehyde dimethylacetal (200 ml), benzylamine (69.2 ml) and potassium hydroxide (74.6 g) was heated at 100° C. for 6 hrs. The reaction solution was cooled down to room temperature and extracted with chloroform. The organic layer was dried over potassium carbonate and the solvent was distilled off. The resultant black oily material was purified by silica gel column chromatography to give 161.13 g of reddish brown oily material (71.4% yield).

$^1$H NMR (CDCl$_3$) δ1.18 (t, J=7 Hz, 12H), 2.74 (d, J=5 Hz, 4H), 3.48 (dq, J=10 Hz, 4H), 3.63 (dq. J=10 Hz, 4H), 3.79 (s, 2H), 4.56 (t, J=5 Hz, 2H), 7.19–7.36 (m, 5H)

ii) Preparation of 3-benzyl-9-methyl-7-oxo-3,9-diazabicyclo[3.3.1]nonane

To N,N-bis(2,2-dimethoxyethyl)benzylamine (80.00 g) were added hydrochloric acid (128 ml) and water (1400 ml) and the mixture was refluxed for 1.5 hrs. This solution was poured into a solution of citric acid (43.46 g), sodium dihydrogen phosphate (92.84 g) and water (1400 ml) and further methylamine hydrochloride (19.09 g) and acetonedicarboxylic acid (48.20 g) were added. The mixture was treated with 40% aqueous sodium hydroxide solution to pH 5.5 and stirred at room temperature for 5 days.

The reaction solution was treated with sodium hydroxide to pH 13 and extracted with chloroform. The organic layer was dried over anhydrous magnesium sulfate and the solvent was distilled off under reduced pressure. The resultant black oily material was purified by silica gel column chromatography to afford the title compound (9.33 g).

iii) Preparation of 3-benzyl-7-hydroxyimino-9-methyl-3,9-diazabicyclo[3.3.1]nonane A mixture of 3-benzyl-9-methyl-7-oxo-3,9-diazabicyclo[3.3.1]nonane (9.33 g), hydroxylamine hydrochloride (3.98 g), pyridine (12.5 ml) and ethanol was heated at reflux for 2 hrs. The reaction solution was cooled down to room temperature, potassium carbonate (15 g) and water (8 ml) were added and the stirring was continued for a while. The resultant suspension was filtered through celite and the solvent was distilled off under reduced pressure. The resulting residue was mixed with chloroform (200 ml) and filtered through Celite. The solvent was distilled off under reduced pressure. The resultant residue was purified by silica gel column chromatography and crystallized to afford the title compound (3.87 g).

$^1$H NMR (CDCl$_3$) 2.26 (d, J=16 Hz, 1H), 2.38 (dd, J=6, 16 Hz, 1H), 2.44–2.52 (m, 2H), 2.56 (s, 3H), 2.60–2.73 (m, 3H), 3.00–3.07 (m, 3H), 3.40 (s, 2H), 7.20–7.31 (m, 5H)

iv) Preparation of endo-7-amino-3-benzyl-9-methyl-3,9-diazabicyclo[3.3.1]nonane

Into an autoclave was charged 3-benzyl-7-hydroxyimino-9-methyl-3,9-diazabicyclo[3.3.1]nonane (3.50 g), ammonium acetate (12.48 g) and Raney Ni (W4) (50 ml) and the content was shaked at 70° C. and at a hydrogen pressure of 120 kg/cm$^2$ for 9 hrs. The reaction solution was filtered through Celite and the filtrate was distilled off under reduced pressure. The residue was mixed with 20% aqueous sodium hydroxide solution (100 ml) and extracted with chloroform. The organic layer was dried over potassium carbonate and the solvent was distilled off, thus giving an oily product (1.54 g). The product was used for subsequent experiment with no purification.

v) Preparation of endo-3-benzyl-9-methyldiazabicyclo[3.3.1]non-7-yl 1H-indazole-3-carboxamide To a crude endo-7-amino-3-benzyl-9-methyl-3,9diazabicyclo[3.3.1]nonane (1.54 g) dissolved in DMF (25 ml) were added diindazolo[2,3-a,2',3'-d]pyrazine-7,14-dione (0.90 g) and DMAP (about 0.06 g) and the mixture was stirred at room temperature overnight. After removing an insoluble material by Celite filtration, the reaction solution was concentrated. Purification of the resultant yellow oily product by silica gel column chromatography gave the title compound (2.36 g).

$^1$H NMR (CDCl$_3$) δ1.46 (d, J=15 Hz, 2H), 2.46 (s, 3H), 2.50–2.43 (m, 2H 2.58 (dd, J=3, 11 Hz, 2H), 2.70 (d, J=11 Hz, 2H), 2.82 (br, 2H), 3.82 (s, 2H), 4.69 (dr, J=7, 7 Hz. 1H), 7.11–7.48 (m, 8H), 8.43 (d, J=5 Hz,

1H), 10.72 (s, 1H), 10.82 (d, J=10 Hz, 1H) m.p. 183°–185° C. (hydrochloride)

EXAMPLE 23 endo-9-Methyl-3,9-diazabicyclo[3.3.1]non-7-yl 1H-indazole-3-carboxamide

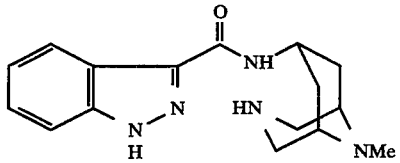

To endo-3-benzyl-9-methyl-3,9-diazabicyclo[3.3.1]-non-7-yl 1H-indazole-3-carboxamide (1.56 g) dissolved in acetic acid (30 ml) was added 10% Pd-C. (6 g) and the mixture was shaked at room temperature for 4 hrs. in the presence of hydrogen gas (at atmospheric pressure). The reaction solution was filtered through Celite and concentrated. The resultant residue was purified by silica gel column chromatography. The resulting solid was triturated with ethyl acetate, filtered to afford the title compound (0.27 g).

$^1$H NMR (CDCl$_3$-CD$_3$OD) δ1.53 (d, J=15 Hz, 2H), 2.52–2.59 (m, 2H), 2.59 (s, 3H), 2.93 (d, J=10 Hz, 4H). 3.33 (dd, J=3, 12Hz, 2H), 4.63 (t, 7Hz, 1H), 7.26 (t, J=8 Hz, 1H), 7.40 (t, J=8 Hz, 1H), 7.52 (d, J=8 Hz, 1H), 8.31 (d, J=8 Hz, 1H)

m.p. 198°–203° C. (hydrochloride)

EXAMPLE 24 endo-9-Benzyl-3-methyl-3,9-diazabicyclo[3.3.1]non-7-yl 1H-indazole-3-carboxamide

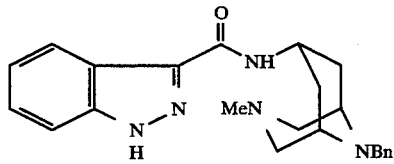

i) Preparation of 9-benzyl-3-methyl-7-oxo-3,9-diazabicyclo[3.3.1]nonane

The title compound was prepared in a similar manner to Example 22, from N, N-his(2, 2-dimethoxyethyl)methylamine, benzylamine and acetonedicarboxylic acid.

$^1$H NMR (CDCl$_3$) δ2.20 (s, 3H), 2.27 (d, J=16 Hz, 2H), 2.44 (dd, J=2, 10 Hz, 2H), 2.55 (d. J=10 Hz, 2H), 2.62 (dd, J=6, 16Hz, 2H), 3.20–3.22 (m 2H), 3.88 (s, 2H), 7.25–7.41 (m, 5H)

ii) 9-Benzyl-7-hydroxyimino-3-methyl-3,9-diazabicyclo-[3.3.1]nonane $^1$H NMR (CDCl$_3$) δ2.17 (s, 3H), 2.26–2.42 (m, 4H), 2.55–2.69 (m, 3H), 3.00–3.04 (m. 311), 3.84 (s. 2H), 7.23–7.39 (m. 5H)

iii) endo-7-Amino-9-benzyl-3-methyl-3,9-diazabicyclo-[3.3.1]noname $^1$H NMR (CDCl$_3$) δ1.34 (d, J=16 Hz. 2H), 2.25 (s, 3H), 2.36 (dd, J=7, 16 Hz, 2H), 2.42 (dd, J=3, 10 Hz, 2H), 2.55 (d, J=10Hz, 2H), 2.78–2.80 (m, 2H), 3.14 (t, J=7 Hz. 1H), 3.78 (s, 2H), 7.20–7.37 (m, 5H)

iv) endo-9-Benzyl-3-methyl-3,9-diazabicyclo[3.3.1]non-7-yl 1H- indazole-3-carboxamide To a solution of endo-7-amino-3-methyl-9-benzyl3,9-diazabicyclo [3.3.1]nonane (3.6 9) in DMF (40 ml) were added diindazolo[2,3-a,2′,3′-d]pyrazine-7,14-dione (2.5 g) and DMAP (0.1 g ) and the mixture was stirred at room temperature for one day. An insoluble material was filtered off and the solvent was distilled off under reduced pressure. The resultant yellow oily material was subjected to silica gel column chromatography (methanol/chloroform) and crystallized from iso-propylether to give the title compound (4.7 g ) as a pale yellow powder (81% yield ).

$^1$H NMR (CDCl$_3$) δ1.49 (d, J=15 Hz, 2H), 2.42 (s, 3H), 2.45 (dd. J=6, 1 5 Hz, 2H), 2.55 (dd, J=3, 11Hz, 2H), 2.68 (d, J=11 Hz, 2H), 2.88 (broad s, 2H), 3.85 (s, 2H), 4.69 (ddd, J=3, 6, 10Hz, 1H), 7.22–7.28 (m, 5H), 7.32 (t, J=7 Hz, 1H), 7.36–7.41 (m, 1H), 7.48 (d. J=8Hz, 1H), 8.45 (d, J=8 Hz, 1H), 10.60 (broad s, 1H), 11.41 (d, J=10 Hz. 1H)

IR (KBr): 3410, 1642, 1542, 1534, 1470, 1158, 918, 758, 702 cm$^{-1}$ (hydrochloride)

m.p. 175°–185° C. (dec., hydrochloride)

EXAMPLE 25 endo-3-Methyl-3,9-diazabicyclo[3.3.1]non-7-yl 1H-indazole-3-carboxamide

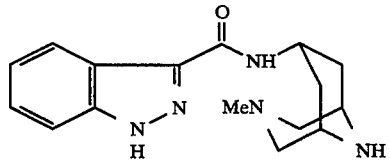

To a solution of endo-9-benzyl-3-methyl-3,9diazabicyclo [3.3.1]non-7-yl 1H-indazole-3-carboxamide (4.0 g) in acetic acid (80 ml ) was added 10% palladium on carbon (16 g ) and the mixture was shaked at room temperature in the presence of hydrogen gas (at atmospheric pressure ) for 30 minutes. The catalyst was filtered off and the solvent was distilled off under reduced pressure. The resultant yellow oily material was chromatographed on silica gel (methanol/methylene chloride/ammonia water) to give the title compound (2. 2 g ) was white powder (74% yield ).

$^1$H NMR (CD$_3$OD) δ1.72 (d. J=14 Hz, 2H), 2.34 (dd, J=7, 14Hz, 2H), 2.41 (dd, J=3, 11 Hz. 21Ḟ), 2.44 (s, 3H), 2.88 (d, J=11 Hz, 2H), 3.14 (broad s, 2H), 4.52 (t, J=7 Hz, 1H), 7.23 (t, J=10 Hz, 1H), 7.39 (t, J=10 Hz, 1H), 8.20 (d. J=10 Hz, 1H), 8.22 (d, J=10 Hz, 1H)

IR (KBr):3425, 1665, 1542, 1162, 755 cm$^{-1}$ (hydrochloride) m.p. 215°–220° C. (dec., hydrochloride)

EXAMPLE 26 endo-3-Allyl-9-methyl-3,9-diazabicyclo[3.3.1]non-7-yl 1H-indazole-3-carboxamide

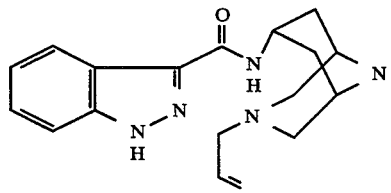

To endo-9-methyl-3,9-diazabicyclo[3.3.1]non-7-yl 1H -indazole-3-carboxamide (0.20g) dissolved in ethylene glycol (5 ml ) was added allyl bromide (1 ml) and the mixture was heated at reflux for 3 hrs. The reaction solution was diluted with chloroform, washed with an aqueous sodium hydroxide solution and water, dried over potassium carbonate and distilled off under reduced pressure. The resultant oily material was purified by silica gel column chromatography to afford the title compound (0.14 g).

¹H NMR (CDCl₃) δ1.42 (d, J=15 Hz, 2H), 2.39-2.51 (m, 4H), 2.46 (s, 3H), 2.71 (d, J=11 Hz, 2H), 2.81-2.84 (m, 2H), 3.07 (d, J=7 Hz, 2H), 4.58-4.65 (m, 1H), 5.00 (d, J=10 Hz, 1H), 5.10 (d, J=17 Hz, 1H), 6.10-6.21 (m, 1H), 7.30 (t, J=8 Hz, 1H), 7.17 (t, J=8 Hz, 1H), 7.40 (d, J=9 Hz, 1H), 8.36 (d, J=8 Hz, 1H), 10.86 (d, J=10 Hz. 1H), 11.40 (s, 1H) m.p. 169°–171° C. (hydrochloride)

EXAMPLE 27 endo-3-(4-Fluorobenzyl)-9-methyl-3,9-diazabicyclo[3.3.1]non-7-yl 1H-indazole-3-carboxamide

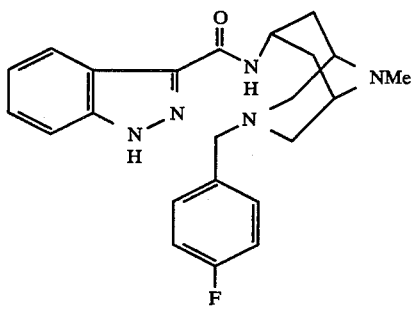

The title compound was prepared in accordance with the procedure outlined in Example 26.

¹H NMR (CDCl₃) δ1.49 (d, J=15 Hz, 2H), 2.51 (s, 3H), 2.53-2.57 (m, 2H), 2.58-2.64 (m, 2H), 2.73 (d, J=11 Hz, 2H), 3.83 (s, 2H), 2.88 (s, 2H), 4.71 (dd, J=7, 10Hz, 1H), 6.83-6.90 (m, 2H), 7.38-7.30 (m, 3H), 7.54-7.42 (m, 2H), 8.47 (d, J=8 Hz, 1H), 10.16 (s, 1H), 10.75 (d, J=10 Hz, m.p. 173°–175° C. (hydrochloride)

EXAMPLE 28 endo-3-Acetyl-9-methyl-3,9-diazabicyclo[3.3.1]non-7-yl 1H-indazola-3-carboxamide

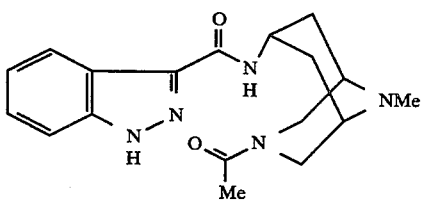

endo-9-Methyl-3,9-diazabicyclo[3.3.1non-7-yl 1H-indazole-3-carboxamide (0.20 g) was suspended in chloroform (10 ml) and triethylamine (0.10 ml) and acetic arthydride (0.07 ml) were added. The mixture was stirred at room temperature for 5 minutes and the solvent was distilled off under reduced pressure. Purification by silica gel column chromatography gave the title compound (0.15 g).

¹H NMR (CDCl₃) δ1.56 (d, J=15 Hz, 1H), 1.69 (d, J=15 Hz, 1H), 2.13 (s, 3H), 2.51 (d, J=8 Hz, 1H), 2.55 (d, J=7 Hz, 1H), 2.58 (s, 3H), 3.11-3.04 (m, 2H), 3.33 (dd, J=3, 13 Hz. 1H), 3.49 (d, J=12 Hz, 1H), 3.65 (dd, J=4, 12 Hz, 1H), 4.18 (d. J=14 Hz. 1H), 4.58-4.55 (m, 1H), 7.20 (t, J=8 Hz, 1H), 7.33 (t, J=8 Hz, 1H), 7.48 (d, J=8 Hz, 1H), 7.67 (d, J=9 Hz, 1H), 8.29 (d, J=8 Hz, 1H), 12.54 (br, 1H)

m.p. 268°–269° C. (hydrochloride)

EXAMPLE 29 endo-3-Isobutyl-9-methyl-3,9-diazabicyclo[3.3.1]non-7-yl 1H-indazole-3-carboxamide

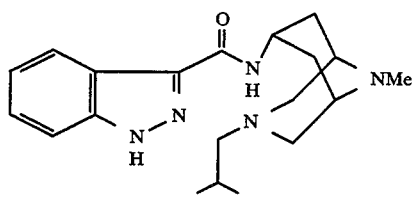

To endo-9-methyl-3,9-diazabicyclo[3.3.1]non-7-yl 1H-indazole-3-carboxamide (0.30 g) dissolved in DMF (7.5 ml) was added isobutyl bromide (2.75 g) and triethylamine (0.11 g) and the mixture was heated at about 80° C. with stirring for 13 hrs. The reaction solution was diluted with chloroform, washed with an aqueous sodium hydroxide solution and water, dried over potassium carbonate and distilled off under reduced pressure. The resultant oily material was purified by silica gel column chromatography to afford the title compound (0.25 g).

¹H NMR (CDCl₃) δ0.78 (d, J=6 Hz, 6H), 1.52 (d, J=15 Hz, 2H), 1.9-2.0 (m, 1H), 2.32 (d, J=7 Hz, 2H), 2.4-2.6 (m, 4H), 2.53 (s, 3H), 2.78 (d, J=11 Hz, 2H), 2.89 (s, 2H), 4.7-4.8 (m, 1H), 7.2-7.5 (m, 3H), 8.34 (d, J=8 Hz, 1H, 10.49 (d, J=10 Hz, 1H), 11.2-11.3 (bs, 1H)

EXAMPLE 30 endo-3-(2-Ethoxyethyl)-9-methyl-3,9-diazabicyclo[3.3.1]non-7-yl 1H-indazole-3-carboxamide

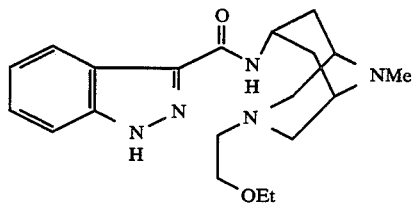

The title compound was prepared in accordance with the procedure outlined in Example 26.

¹H NMR (CDCl₃) δ1.16 (t, J=7 Hz, 3H), 1.47 (d, J=15 Hz, 2H), 2.4-3.0 (m, 10H), 2.53 (s, 3H), 3.44 (q. J=7 Hz, 2H), 3.79 (d, J=6 Hz, 2H), 4.6-4.7 (m, 1H), 7.2-7.5 (m, 3H), 8.42 (d, J=8 Hz, 1H), 10.91 (d, J=10 Hz, 1H), 11.0-11.1 (bs, 1H)

EXAMPLE 31

N-(endo-3,9-Dimethyl-3,9-diazabicyclo[3-3-1]non-7-yl) N-methyl 1-methylindazole-3-carboxamide

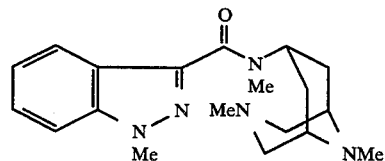

To endo-3,9-dimethyl-3,9-diazabicyclo[3.3.1]non-7yl 1H-indazole-3-carboxamide (1.00 g, 3.19 mmol) dissolved in dry THF (30 ml) was added under argon gas stream 1.6 M n-butyl lithium hexane solution (10.2 ml). Further, iodomethane (1 ml) was added dropwise and the mixture was reacted at room temperature for 2 hrs. The reaction mixture was extracted with chloroform and the organic layer was dried and distilled off under reduced pressure. Purification of the residue by silica gel column chromatography gave the title compound.

$^1$N NR (CDCl$_3$) δ1.20–1.36 (m, 2H), 2.22 (s. 2H), 1.80–3.10 (m, 8H), 3.13 (s, 3H), 4.05 (s, 3H), 5.26–5.40 (m, 1H), 6.88–7.56 (m, 4H) Pharmacological Test on 5-HT$_3$ Receptor Antagonist Activity Temporary bradycardia is induced by administration of 5-HT (serotonin) to anaesthetised rats via jugular vein (yon Bezold Jarisch Reflex) (A. S. Paintal, Physiol. Rev., 53, 159–210 (1973)). Richardson B. P. et al have proved in Nature, 316, 126–131 (1985) that the 5-HT-induced reflex occurs through 5-HT$_3$receptors. Thus the 5-HT$_3$ receptor antagonist activity of the present compounds can be demonstrated by inhibition of said reflex.

The compounds of the present invention were evaluated for antagonism of the yon Bezold-Jarisch reflex induced by 5-HT in the anaesthetised rat according to the following method.

Rats were anaesthetised with urethane (1 g/kg, intraperitoneally) and blood pressure and heart rate recorded from left femoral artery. Percent inhibition was calculated from bradycardia induced by 5-HT (30 μg/kg) given 5 minutes following intrajugular administration of a compound of the invent ion, taking the bradycardia induced by the intrajugular administration of 5-HT. The compounds of the present invention were tested in the form of their hydrochloride salts. The results are shown below.

| Compounds of Example | Percent Inhibition (%) Concentration of test compound (μg/kg, i.v.) | | | |
|---|---|---|---|---|
| | 0.01 | 0.1 | 1.0 | 10 |
| 2 | 11 | 86 | | |
| 3 | | 13 | 70 | |
| 4 | | 60 | | |
| 5 | | 29 | 44 | 91 |
| 6 | | 19 | 35 | 87 |
| 7 | | 30 | 83 | |
| 8 | | 48 | 100 | |
| 9 | 14 | 41 | 96 | |
| 10 | | 37 | 100 | |
| 11 | | 39 | 53 | |
| 12 | 45 | 57 | 72 | |
| 13 | | 27 | 71 | |
| 14 | | 18 | 97 | |
| 15 | | 47 | | |
| 16 | | 34 | | 88 |
| 17 | 33 | 53 | | |
| 18 | | 23 | 53 | |
| 19 | 40 | 59 | | |
| 20 | 51 | 73 | | |
| 21 | 21 | 38 | 85 | |
| 22 | | 48 | 87 | |
| 23 | | 28 | 82 | |
| 24 | | 35 | | |
| 25 | | 21 | | |
| 26 | | 38 | | |
| 27 | | 75 | 98 | |
| 28 | | 23 | 71 | |
| 29 | 27 | 81 | | |
| 30 | | 52 | 100 | |

The following examples illustrate pharmaceutical formulations according to the invention.

| Tablets (per tablet) | |
|---|---|
| Compound of Example 9 (hydrochloride) | 1 mg |
| Lactose | 70 mg |
| Crystalline cellulose | 20 mg |
| Corn starch | 8 mg |
| Magnesium stearate | 1 mg |

The above ingredients were uniformly blended to prepare powders for direct compression. The powders were formed in a rotary tabletting machine to tablets each 6 mm in diameter and weighing 100 mg.

| Granules (per divided packet) | |
|---|---|
| Compound of Example 10 (hydrochloride) | 1 mg |
| Lactose | 99 mg |
| Crystalline cellulose | 50 mg |
| Corn starch | 50 mg |
| Hydroxypropylcellulose | 10 mg |
| Ethanol | 9 mg |

The compound, lactose, corn starch and crystalline cellulose were uniformly blended and a solution of hydroxypropylcellulose in ethanol was added. The mixture was kneaded and granulated by an extrusion granulation method. The granules were then dried in a drier at 50° C. The dried granules were screened to granule sizes between 297 μm and 1460 μm to give a granule formulation weighing 200 mg per divided packet.

| Syrups | |
|---|---|
| Compound of Example 12 (hydrochloride) | 0.100 g |
| Refined sugar | 30.000 g |
| D-sorbitol, 70 W/V % | 25.900 g |
| Ethyl paraoxybenzoate | 0.030 g |
| Propyl paraoxy benzoate | 0.015 g |
| Flavor | 0.200 g |
| Glycerin | 0.150 g |
| 96% Ethanol | 0.500 g |
| Distilled water | q.s. |

The compound, refined sugar, D-sorbitol, ethyl paraoxybenzoate and propyl paraoxybenzoate were dissolved in 60 g of warm water. After cooling, glycerin and a solution of the flavor in ethanol were added. Distilled water was added to the mixture to make up a total amount of 100 ml.

| Injections | |
|---|---|
| Compound of Example 15 (hydrochloride) | 0.1 mg |
| Sodium chloride | 10 mg |
| Distilled water | q.s. |

The compound and sodium chloride were dissolved in distilled water to make up a total amount of 1.0 ml.

What is claimed is:

1. A compound of formula (I) or a pharmaceutically acceptable salt thereof:

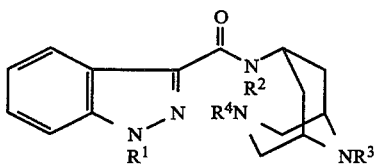

wherein $R^1$ is hydrogen, $C_1$-$C_{10}$ alkyl, ($C_3$-$C_{10}$)alkenyl, ($C_3$-$C_6$)alkynyl, cyclo($C_3$-$C_7$)alkyl, cyclo($C_3$-$C_6$)alkyl($C_1$-$C_4$)alkyl, ($C_1$-$C_6$) alkoxy($C_2$-$C_6$)alkyl, oxo($C_3$-$C_6$)alkyl, ($C_1$-$C_6$)alkoxycarbonyl ($C_1$-$C_4$)alkyl, ($C_1$-$C_4$)alkyl, ($C_1$-$C_6$)alkoxycarbonyl, alkanoyl, benzoyl, di($C_1$-$C_6$)alkylamino($C_2$-$C_6$)alkyl, hydroxy($C_2$-$C_6$)alkyl, halo($C_2$-$C_6$)alkyl, cyano($C_1$-$C_4$)alkyl, piperidinyl, pyrrolidinyl, aryl, heteroaryl($C_1$-$C_4$)alkyl wherein the heteroaryl moiety is a 5-6 membered ring having 1-3 nitrogen atoms in the ring optionally fused with a benzene ring or aryl($C_1$-$C_4$)alkyl, the aryl group and the aryl moiety being optionally substituted by $C_1$-$C_6$ alkoxy, nitro, $C_1$-$C_6$ alkyl, amino or halo;

$R^2$ is hydrogen or $C_1$-$C_{10}$ alkyl;

$R^3$ and $R^4$ may be the same or different and each is hydrogen, $C_1$-$C_{10}$ alkyl, $C_2$-$C_{10}$ alkenyl, alkanoyl, benzoyl, ($C_1$-$C_6$)alkoxy($C_2$-$C_6$) alkyl or aryl($C_1$-$C_6$)alkyl wherein the aryl moiety is optionally substituted by $C_1$-$C_6$ alkoxy, nitro, $C_1$-$C_4$ alkyl, amino or halo;

with the proviso that when $R^2$ is hydrogen and both $R^3$ and $R^4$ are $C_1$-$C_{10}$ alkyl, $R^1$ does not represent hydrogen, $C_1$-$C_{10}$ alkyl, aralkyl or dimethylamino($C_2$-$C_6$)alkyl.

2. A compound of claim 1 wherein $R^1$ is phenyl or naphthyl substituted by $C_1$-$C_6$ alkoxy, nitro, $C_1$-$C_6$ alkyl, amino or halo.

3. A compound of claim 1 wherein $R^1$ is aryl($C_1$-$C_4$) alkyl substituted by $C_1$-$C_6$ alkoxy, nitro, $C_1$-$C_6$ alkyl, amino or halo.

4. A compound of claim 1 wherein $R^3$ and $R^4$ are each phenyl or naphthyl($C_1$-$C_6$)alkyl substituted by $C_1$-$C_6$ alkoxy, nitro, $C_1$-$C_6$ alkyl, amino or halo.

5. A pharmaceutical composition which comprises a compound or a pharmaceutically acceptable salt thereof as defined in any one of claims 2, 3, 4 or 1 and a pharmaceutically acceptable carrier.

* * * * *

UNITED STATES PATENT AND TRADEMARK OFFICE
CERTIFICATE OF CORRECTION

PATENT NO. : 5,344,831
DATED : September 6, 1994
INVENTOR(S) : Hiroaki SATOH et al.

It is certified that error appears in the above-identified patent and that said Letters Patent is hereby corrected as shown below:

Column 27, lines 12-13, change "cyclo($C_3$14 $C_6$)" to --cyclo($C_3$-$C_6$)--.

Column 27, lines 14-15, delete "$C_1$-$C_4$)alkyl".

Signed and Sealed this

Twenty-first Day of February, 1995

BRUCE LEHMAN

*Attest:*

*Attesting Officer*  *Commissioner of Patents and Trademarks*